(12) United States Patent
Kwiatkowski et al.

(10) Patent No.: US 7,034,040 B2
(45) Date of Patent: *Apr. 25, 2006

(54) FLUORINATED HETEROCYCLIC COMPOUNDS AND METHODS OF SYNTHESIS

(75) Inventors: Stefan Kwiatkowski, Lexington, KY (US); Miroslaw Golinski, Lexington, KY (US)

(73) Assignee: R.T. Alamo Ventures I, Beverly Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/849,606

(22) Filed: May 20, 2004

(65) Prior Publication Data

US 2005/0032833 A1    Feb. 10, 2005

Related U.S. Application Data

(63) Continuation of application No. 10/281,801, filed on Oct. 28, 2002, now Pat. No. 6,767,914.

(60) Provisional application No. 60/361,150, filed on Mar. 1, 2002.

(51) Int. Cl.
*A61K 31/47* (2006.01)
*C07D 215/22* (2006.01)

(52) U.S. Cl. ..................... 514/312; 546/155

(58) Field of Classification Search ............... 514/312; 546/155

See application file for complete search history.

(56) References Cited

U.S. PATENT DOCUMENTS

| | | | |
|---|---|---|---|
| 6,110,489 A | 8/2000 | Cutler | 424/449 |
| 6,132,753 A | 10/2000 | Cutler | 424/423 |
| 6,194,433 B1 | 2/2001 | Cutler | 514/312 |
| 6,258,373 B1 | 7/2001 | Cutler | 424/434 |
| 6,451,813 B1 | 9/2002 | Cutler et al. | 514/312 |
| 6,767,914 B1 * | 7/2004 | Kwiatkowski et al. | 514/312 |

FOREIGN PATENT DOCUMENTS

WO    WO 99/56666    11/1999

* cited by examiner

*Primary Examiner*—Charanjit S. Aulakh
(74) *Attorney, Agent, or Firm*—Medlen & Carroll, LLP

(57) ABSTRACT

Compositions of the present invention comprise fluorinated heterocyclic compounds, including monofluoroflosequinan and difluoroflosequinan. The methods of the present invention comprise the synthesis of monofluoroflosequinan and difluoroflosequinan.

2 Claims, 8 Drawing Sheets

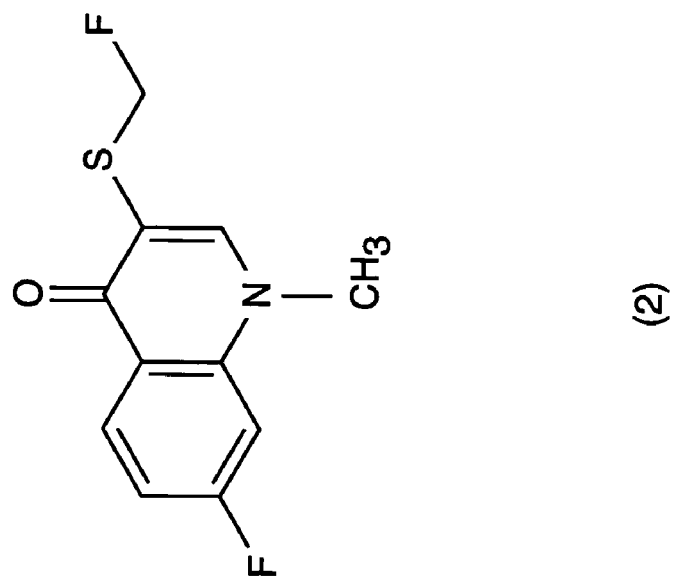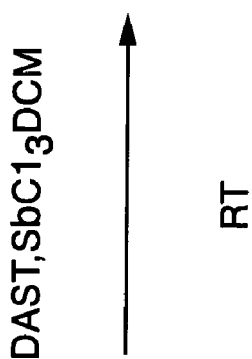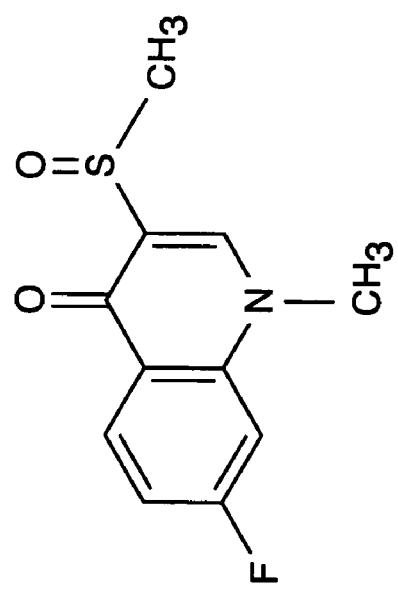
FIG. 3

FIG. 5

| CAT.# | TARGET | BATCH♠ | SPP. | n= | CONC. | †%INHIBITION % | -100 -50 0 50 100 | IC$_{50}$ | K$_1$ | n$_H$ | R |
|---|---|---|---|---|---|---|---|---|---|---|---|
| 146000 | PHOSPHODIESTERASE PDE1 | 45373 | bov | 2 | 100µM | 29 | | | | | |
| 148000 | PHOSPHODIESTERASE PDE2 | 45375 | hum | 2 | 100µM | 10 | | | | | |
| 152000 | PHOSPHODIESTERASE PDE3 | 45376 | hum | 2 | 100µM | 2 | | | | | |
| 154000 | PHOSPHODIESTERASE PDE4 | 45253 | hum | 2 | 100µM | 12 | | | | | |
| 156000 | PHOSPHODIESTERASE PDE5 | 45452 | hum | 2 | 100µM | 4 | | | | | |
| 156100 | PHOSPHODIESTERASE PDE6 | 45453 | bov | 2 | 100µM | 23 | | | | | |
| 180010 | PROTEIN SERINE/THREONINE KINASE PKCα | 45273 | hum | 2 | 1000µM | 10 | | | | | |
| 178010 | PROTEIN SERINE/THREONINE KINASE PKC, NON-SELECTIVE | 45090 | rat | 2 | 1000µM | 74 | | | | | |
| ♦ | | 45491 | rat | 2 | 300µM | 54 | | | | | |
| ♦ | | | | 2 | 100µM | 50 | | | | | |
| 214510 | CALCIUM CHANNEL TYPE L, BENZOTHIAZEPINE | 45139 | rat | 2 | 1000µM | 13 | | | | | |
| 214600 | CALCIUM CHANNEL TYPE L, DIHYDROPYRIDINE | 45167 | rat | 2 | 1000µM | 27 | | | | | |
| 215000 | CALCIUM CHANNEL TYPE L, PHENYLALKYLAMINE | 45262 | rat | 2 | 1000µM | 7 | | | | | |
| 242500 | INOSITOL TRIPHOSPHATE IP$_3$ | 45039 | rat | 2 | 1000µM | 17 | | | | | |

♠BATCH: REPRESENTS COMPOUNDS TESTED CONCURRENTLY IN THE SAME ASSAY(S).
♦DENOTES ITEM MEETING CRITERIA FOR SIGNIFICANCE
†RESULTS WITH ≥ 50% STIMULATION OR INHIBITION ARE BOLDFACED.
(NEGATIVE VALUES CORRESPOND TO STIMULATION OF BINDING ENZYME ACTIVITY)
R=ADDITIONAL COMMENTS   bov=BOVINE; hum=HUMAN

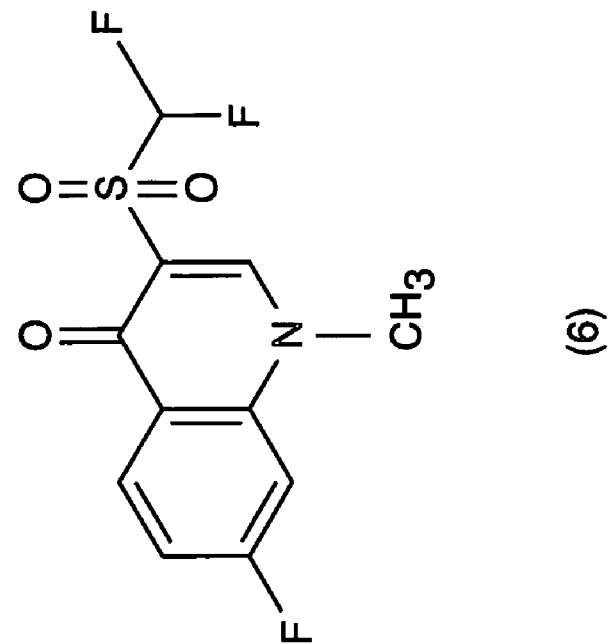
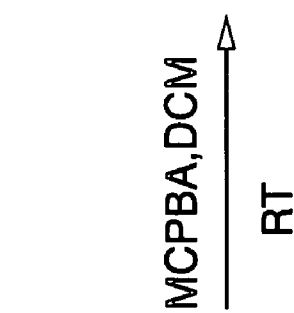
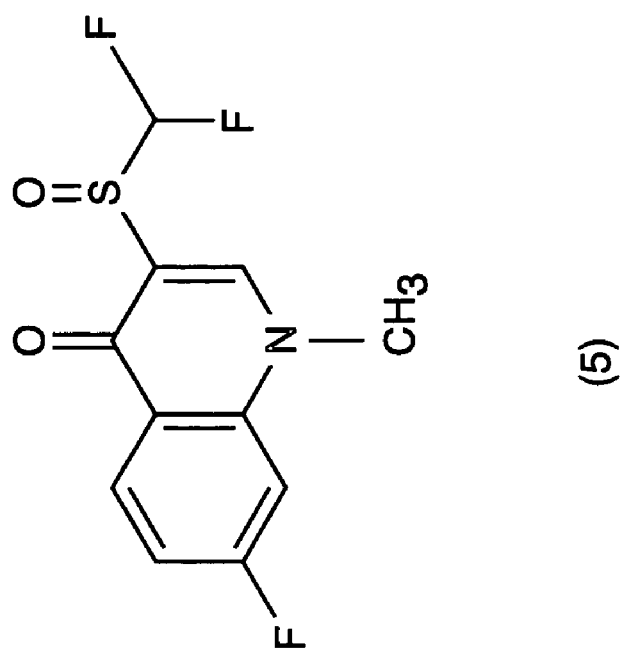
FIG. 6

FLUORINATED HETEROCYCLIC COMPOUNDS AND METHODS OF SYNTHESIS

This is a Continuation patent application which claims priority to U.S. patent application Ser. No. 10/281,801, filed on Oct. 28, 2002, which subsequently issued as U.S. Pat. No. 6,767,914 B2, which claimed priority to Provisional U.S. patent application Ser. No. 60/361,150, filed on Mar. 01, 2002.

FIELD OF THE INVENTION

The present invention teaches the synthesis of fluorinated heterocyclic compounds. The present invention also contemplates composition comprising fluorinated heterocyclic compounds.

BACKGROUND

A variety of heterocyclic compounds have been described as having various pharmaceutical applications. However, the synthesis of such compounds, especially on a large scale, is often labor-intensive, expensive and time consuming. What is needed therefore, is a simplified and economical method for the synthesis and purification of fluorinated heterocyclic compounds.

SUMMARY OF THE INVENTION

In one embodiment, the present invention contemplates compositions comprising racemic monofluoroflosequinan (7-fluoro-3-fluoromethylsulfinyl-1-methyl-4-quinolone).

In one embodiments, the present invention contemplates compositions comprising difluoroflosequinan (3-difluoromethylsulfinyl-7-fluoro-1-methyl-4-quinolone). In another other embodiments, the present invention contemplates compositions comprising the sulfone derivative of difluoroflosequinan.

In one embodiment, the present invention contemplates methods for the synthesis of racemic monofluoroflosequinan. In one embodiment, the method comprises: a) providing: i) 7-fluoro-3-fluoromethylthio-1-methyl-4-quinolone and ii) m-chloroperbenzoic acid (MCPBA); and b) reacting said 7-fluoro-3-fluoromethylthio-1-methyl-4-quinolone and m-chloroperbenzoic acid in a solvent under conditions such that 7-fluoro-3-fluoromethylsulfinyl-1-methyl-4-quinolone is produced. In some embodiments, the solvent is dichloromethane (DCM). In another embodiment, a method of synthesis of 7-fluoro-3-fluoromethylthio-1-methyl-4-quinolone is contemplated. In one embodiment, the method comprises: a) providing: i) 7-fluoro-1-methyl-3-methylsulfinyl-4-quinolone (flosequinan), and ii) (diethylamino)sulfur trifluoride (DAST); and b) reacting said flosequinan and (diethylamino)sulfur trifluoride in a solvent under conditions such that 7-fluoro-3-fluoromethylthio-1-methyl-4-quinolone is produced. In some embodiments, the solvent is dichloromethane (DCM). In some embodiments, a catalyst is provided. The reaction time of step b) is reduced in the presence of the catalyst. In some embodiments, the catalyst is antimony chloride ($SbCl_3$).

In one embodiment, the present invention contemplates methods of synthesis of difluoroflosequinan (3-difluoromethylsulfinyl-7-fluoro-1-methyl-4-quinolone). In one embodiment, a second fluorine atom is introduced onto a side chain of 7-fluoro-3-fluoromethylthio-1-methyl-4-quinolone, to produce 3-difluoromethylthio-7-fluoro-1-methyl-4-quinolone, which is subsequently oxidized to produce 3-difluoromethylsulfinyl-7-fluoro-1-methyl-4-quinolone. In one embodiment, the method comprises: a) providing (i) 7-fluoro-3-fluoromethylthio-1-methyl-4-quinolone, (ii) SELECTFLUOR and (iii) triethylamine and b) reacting said 7-fluoro-3-fluoromethylthio-1-methyl-4-quinolone, SELECTFLUOR and triethylamine in a solvent under conditions such that 3-difluoromethylthio-7-fluoro-1-methyl-4-quinolone is produced and c) further reacting said 3-difluoromethylthio-7-fluoro-1-methyl-4-quinolone with m-chloroperbenzoic acid (MCPBA) in a solvent under conditions such that 3-difluoromethylsulfinyl-7-fluoro-1-methyl-4-quinolone is produced. In some embodiments, the solvent in step b) is acetronitrile. In some embodiments, the solvent in step c) is dichloromethane (DCM)

DESCRIPTION OF THE DRAWINGS

FIG. 3 depicts the chemical synthesis of 7-fluoro-3-fluoromethylthio-1-methyl-4-quinolone in the presence of a catalyst (Antimony chloride).

FIG. 5 depicts the results of enzyme inhibition and radioligand binding assays with monofluoroflosequinan.

FIG. 6 depicts the synthesis of a sulfone derivative of difluoroflosequinan corresponding to the chemical composition designated as 3-difluoromethylsulfonyl-7-fluoro-1-methyl-4-quinolone.

DEFINITIONS

Figure 1A:
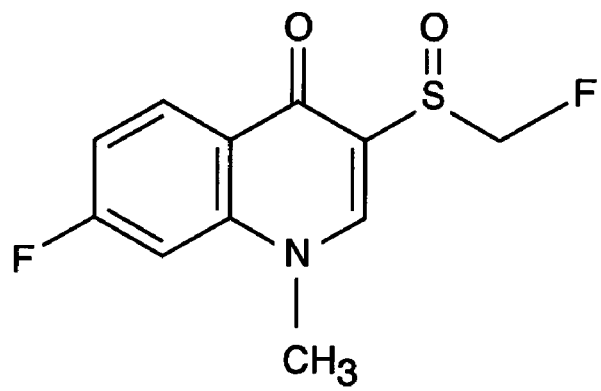
FIG. 1A depicts the chemical structure of 7-fluoro-3-fluoromethylsulfinyl-1-methyl-4-quinolone (monofluoroflosequinan).
Figure 1B:
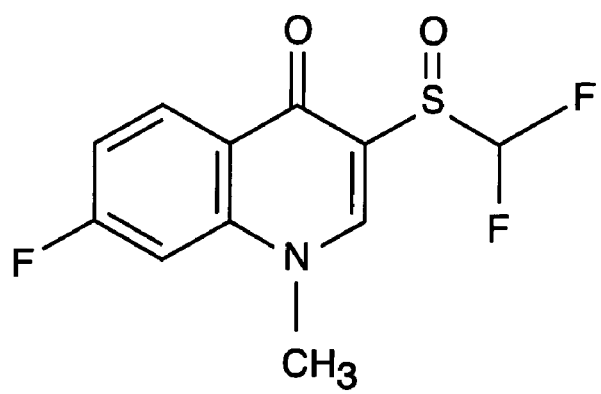
FIG. 1B depicts the chemical structure of 3-difluoromethylsulfinyl-7-fluoro-1-methyl-4-quinolone (difluoroflosequinan).

As used herein, the phrases "flosequinan", "racemic flosequinan", and "flosequinan racemate" refer to (+/−)-7-fluoro-1-methyl-3-(methylsulfinyl)-4(1H)-quinolinone which may also be described as (+/−)-7-fluoro-1-methyl-3-(methylsulfinyl)-4(1H)-quinolone) and as 7-fluoro-1-methyl-3-methyl-sulfinyl-4-quinolone having the chemical structure of:

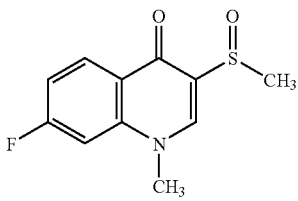

As used herein monofluoroflosequinan refers to the chemical composition designated as 7-fluoro-3-fluoromethylsulfinyl-1-methyl-4-quinolone having the chemical structure corresponding to the structure depicted below:

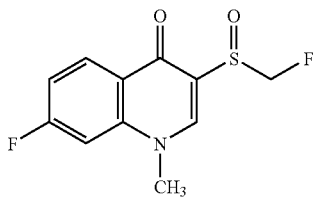

As used herein, "difluoroflosequinan" refers to the chemical composition designated as 3-difluoromethylsulfinyl-7-fluoro-1-methyl-4-quinolone having the chemical structure corresponding to:

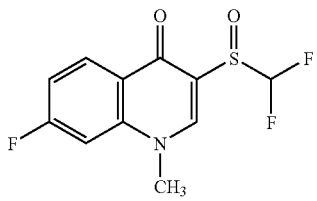

As used herein, the "sulfone derivative of difluoroflosequinan" refers to the chemical composition designated as 3-difluoromethylsulfonyl-7-fluoro-1-methyl-4-quinolone having the chemical structure corresponding to:

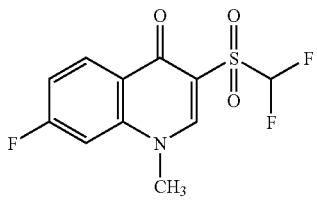

As used herein, "room temperature", "RT" or "ambient temperature" is approximately 18° C. to 25° C.

As used herein, "overnight" is approximately 8 hours, more preferably approximately 12 hours, more typically approximately 17 hours, but can be up to approximately 30 hours.

As used herein, a "heterocyclic" compound refers to a compound comprising a ring composed of atoms of more than one kind.

As used herein, a "catalyst" refers to a substance that, when added to a reaction mixture, changes (e.g., speeds up) the rate of attainment of equilibrium in the system without itself undergoing a permanent chemical change. Examples of suitable catalysts contemplated for use in the present invention include, but are not limited to, antimony chloride and carbon tetrabromide.

As used herein, a "solvent" refers to a substance that will dissolve other substances. An "organic solvent" is an organic substance that will dissolve other substances. Examples of solvents suitable for use in embodiments of the present invention include, but are not limited to dichloromethane and acetonitrile.

As used herein, the term "IBMX" corresponds to the structure having the chemical formula: 3-isobutyl-1-methylxanthine (available from Sigma).

DETAILED DESCRIPTION OF THE INVENTION

In some embodiments, the compositions comprise racemic monofluoroflosequinan. In other embodiments, the compositions comprise racemic difluoroflosequinan, including derivatives thereof. In one embodiment, said difluoroflosequinan derivative is the sulfone derivative of difluoroflosequinan.

Methods of producing a racemic mixture of flosequinan, as set out in U.S. Pat. Nos. 5,079,264 and 5,011,931 to MacLean et al., are hereby incorporated by reference. In one embodiment, racemic flosequinan is prepared according to the protocol set out in Example 4.

Without limiting the invention to any particular mechanism, monofluoroflosequinan and difluoroflosequinan are enzyme inhibitors. In a specific example, monofluoroflosequinan and difluoroflosequinan inhibit protein kinase C (herein after PKC). In another example, difluoroflosequinan (and its sulfone derivative) inhibit phosphodiesterases (herein after PDE). This effect of monofluoroflosequinan and difluoroflosequinan on enzyme activity, more particularly on PKC and PDE, has utility in therapeutics.

The present invention also contemplates the formulation of monofluoroflosequinan, difluoroflosequinan, and the sulfone derivative difluoroflosequinan as a pharmaceutically acceptable salt. In addition, pharmaceutical formulations of monofluoroflosequinan, difluoroflosequinan, and the sulfone derivative difluoroflosequinan may also contain binders, fillers, carriers, preservatives, stabilizing agents, emulsifiers, buffers and excipients as, for example, pharmaceutical grades of mannitol, lactose, starch, magnesium stearate, sodium saccharin, cellulose, and magnesium carbonate. The present invention also contemplates the administration of monofluoroflosequinan, difluoroflosequinan, and the sulfone derivative difluoroflosequinan as a pharmaceutically acceptable salt or formulation. The present invention also contemplates the administration of dichloroflosequinan and monofluoroflosequinan, difluoroflosequinan, and the sulfone derivative difluoroflosequinan formulations to a subject.

Synthesis of Racemic Monofluoroflosequinan and Racemic Difluoroflosequinan

Figure 2:
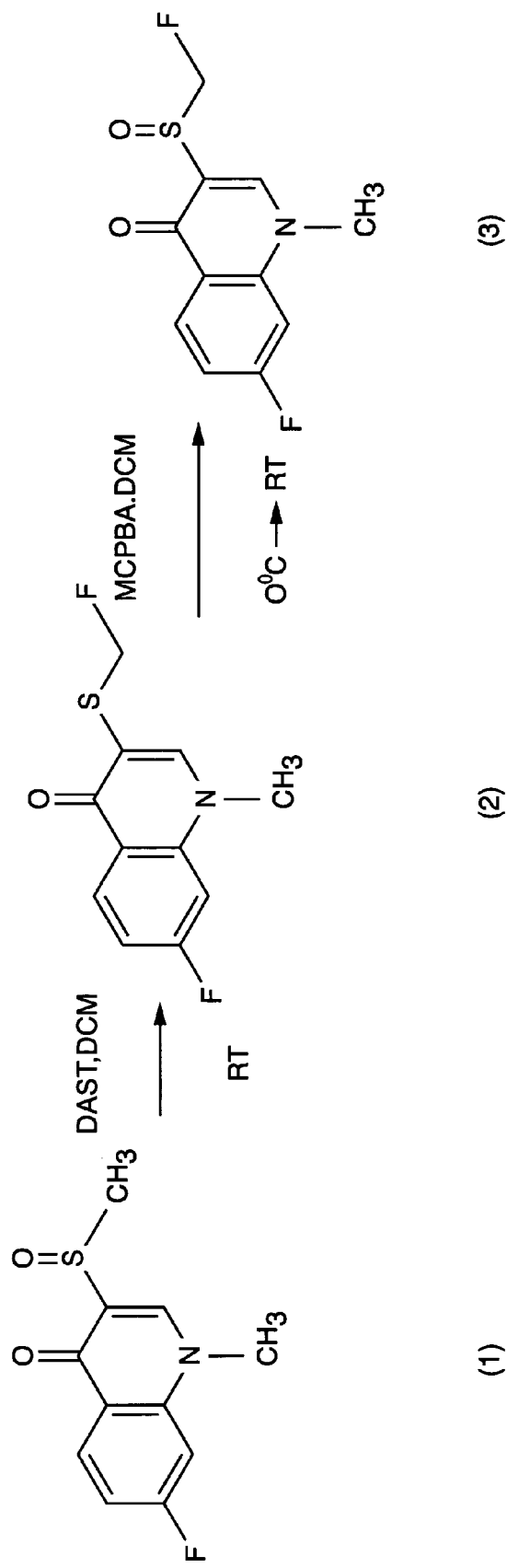
FIG. 2 depicts the steps in the chemical synthesis of 7-fluoro-3-fluoromethylsulfinyl-1-methyl-4-quinolone. Flosequinan (1) is reacted as described to generate 7-fluoro-3-fluoromethylthio-1-methyl-4-quinolone (2). 7-Fluoro-3-fluoromethylthio-1-methyl-4-quinolone (2) is reacted as described to generate 7-fluoro-3-fluoromethylsulfinyl-1-methyl-4-quinolone (3).

The synthesis of monofluoroflosequinan was carried out in two stages (see FIG. 2). Briefly, in the first stage, flosequinan was fluorinated by DAST in DCM at room temperature. This reaction was accompanied by the deoxygenation of the sulfoxide to the sulfide. In the second stage, MCPBA was used to oxidize the sulfide back to the sulfoxide.

In the first stage, DAST was added to a solution of flosequinan in DCM at 20° C. The mixture was stirred at room temperature (25° C.) for three days, then diluted with ether. In a preferred embodiment, the time required for this conversion can be reduced by the use of a suitable catalyst, including but not limited to antimony chloride ($SbCl_3$). In one embodiment, antimony chloride was used and the reaction time was 7 hours (see FIG. 3).

Figure 4:
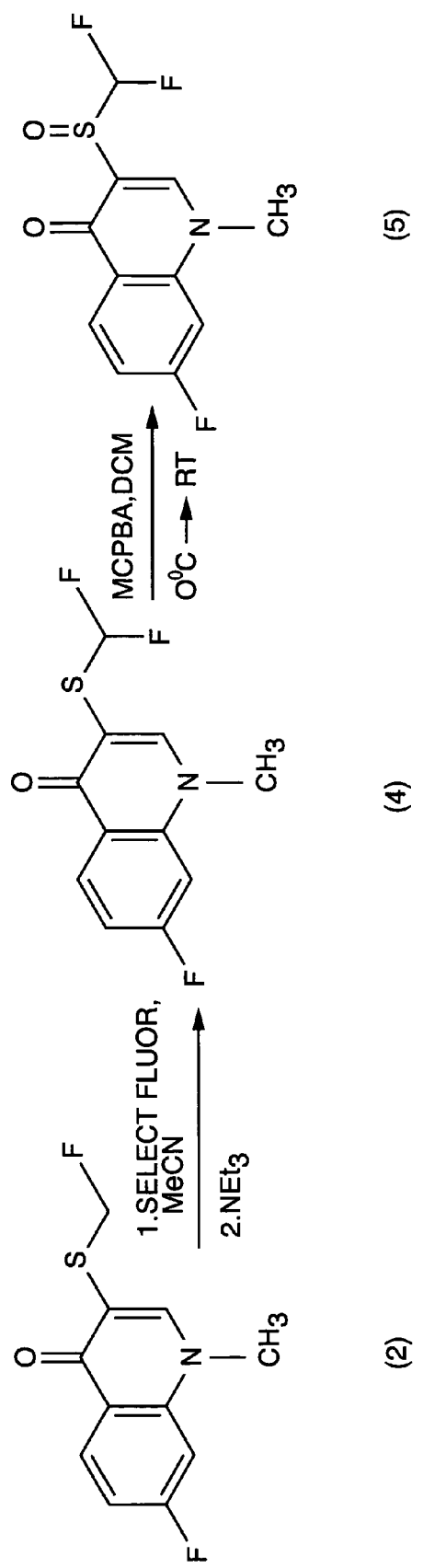
FIG. 4 depicts the steps in the chemical synthesis of 3-difluoromethylsulfinyl-7-fluoro-1 -methyl-4-quinolone (5). 7-fluoro-3-fluoromethylthio-1-methyl-4-quinolone (2) is reacted as described to generate 3-difluoromethylthio-7-fluoro-1-methyl-4-quinolone (4). 3-difluoromethylthio-7-fluoro-1-methyl-4-quinolone (4) is reacted as described to generate 3-difluoromethylsulfinyl-7-fluoro-1-methyl-4-quinolone (5).

Since a few attempts to further fluorinate α-fluorosulfoxide (monofluoroflosequinan) were unsuccessful, the second fluorine atom was introduced into a side chain at an intermediate sulfide stage (see FIG. 4). Specifically, α-fluorosulfide (7-fluoro-3-fluoromethylthio-1-methyl-4-quinolone) was fluorinated with SELECTFLUOR to give a complicated mixture, but a triplet in the $^1$H NMR spectrum (δ=7.10 ppm, J=58.9 Hz) was assigned to α,α-difluorosulfide (3-difluoromethylthio-7-fluoro-1-methyl-4-quinolone). The mixture was subsequently oxidized with MCPBA, to secure the desired α,α-sulfoxide (3-difluoromethylsulfinyl-7-fluoro-1-methyl-4-quinolone), although in low total yield. The fluorination reaction was not optimized.

Synthesis of Difluoroflosequinan Sulfone

Difluoroflosequinan sulfone (3-difluoromethylsulfonyl-7-fluoro-1-methyl-4-quinolone) was prepared by MCPBA oxidation of difluoroflosequinan (3-difluoromethylsulfinyl-7-fluoro-1-methyl-4-quinolone). This synthesis is described in experimental Example 6 and is depicted in FIG. 6.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); L (liters); ml (milliliters); μl (microliters); cm (centimeters); mm (millimeters); μm (micrometers); nm (nanometers); ° C. (degrees Centigrade); mp (melting point).

In Examples 1–4, unless otherwise stated, the source for the chemical reagents was Aldrich, Milwaukee, Wis., USA (unless a reagent was synthesized de novo as described in the examples). In examples 1–3, flosequinan was synthesized according to the protocol provided in example 4, unless otherwise stated.

Example 1

Synthesis of racemic monofluoroflosequinan.

This overall synthetic scheme is described in more detail according to the following reactions. For the purpose of this example, all bracketed numbers [e.g., "(1)"], after the chemical name of a compound, refer to the corresponding chemical structure as designated by the same bracketed number in FIG. 2. The synthesis of 7-fluoro-3-fluoromethylsulfinyl-1-methyl-4-quinolone (3) (monofluoroflosequinan) was carried out in two stages (see FIG. 2).

In the first stage, into a solution of 1.017 g (4.25 mmol) of 7-fluoro-1-methyl-3-methylsulfinyl-4-quinolone (1) in 17 ml of dichloromethane (DCM), 0.758 ml (925 mg, 5.74 mmol) of (diethylamino)sulfur trifluoride (DAST) was added at 20° C. The mixture was stirred at 25° C. for 3 days and then diluted with 40 ml of ether. The precipitated 688 mg (67%) of 7-fluoro-3-fluoromethylthio-1-methyl-4-quinolone (2) was filtered off. An additional 177 mg (17%) of the product (2) was collected after diluting the filtrate with 60 ml of ether. 1H NMR, $CDCl_3$; δ=3.80 s, 3H, N-$CH_3$; 5.69 d, 2H, J=52.8 Hz, $CH_2$; 7.08 dd, 1H, J=10.2 & 2.4 Hz, H at C8, 7.18 ddd, 1H, J=8.8, 7.9 & 2.2 Hz, H at C6; 8.00 s, 1H, H at C2; 8.51 dd, 1H, J=9.0 & 6.3 Hz, H at C5.

The crude product (2) was used in the second stage. To a stirred solution of 673 mg (2.873 mmol) of compound (2) in 80 ml DCM, ~80%, m-chloroperbenzoic acid (MCPBA) (620 mg, 2.873 mmol) was added in a few portions over a period of 1 minute at 0° C. The stirred mixture was allowed to warm to room temperature, was stirred for one hour and then an additional 18 mg of MCPBA was added to complete the transformation. After 30 minutes stirring at room temperature the reaction solution was washed with 15 ml of 5% aqueous sodium carbonate. The aqueous layer was extracted two times with 60 ml of DCM each and the combined DCM solutions were dried over sodium sulfate and concentrated. The residue 660 mg was chromatographed on silica gel with hexane-ethyl acetate (gradient 1:1, 2:3, 1:2) to give 358 mg (50% yield) of racemic 7-fluoro-3-fluoromethylsulfinyl-1-methyl-4-quinolone (3) (monofluoroflosequinan) as a white solid. 1H NMR, $CDCl_3$; δ=3.93 s, 3H, N-$CH_3$; 5.75, 5.73, 5.59, 5.56, 5.46, 5.43, 5.30, 5.27 (8 lines, AB part of ABX), 2H, $CH_2$; 7.18-7.30 m, 2H, H at C8 & C6; 7.98 s, 1H, H at C2; 8.44 dd, 1H, J=9.0 & 6.3 Hz, H at C5.

Example 2

Synthesis of 7-fluoro-3-fluoromethylthio-1-methyl-4-quinolone (Stage One of the synthesis of monofluoroflosequinan) using a catalyst.

This overall synthetic scheme is described in more detail according to the following reactions. For the purpose of this example, all bracketed numbers [e.g., "(1)"], after the chemical name of a compound, refer to the corresponding chemical structure as designated by the same bracketed number in FIG. 3. This example presents the synthesis and results of a representative experiment.

Into a solution of 3.00 g (12.54 mmol) of 7-fluoro-1-methyl-3-methylsulfinyl-4-quinolone (1) and 28.6 mg (0.125 mmol) of antimony chloride ($SbCl_3$) in 40 ml of dichloromethane (DCM), 2.24 ml (2.73 g, 16.92 mmol) of (diethylamino)sulfur trifluoride (DAST) was added at 20° C. The mixture was stirred at 25° C. for 7 hours and then diluted with 70 ml of ether. The precipitated 0.783 g (26%) of 7-fluoro-3-fluoromethylthio-1-methyl-4-quinolone (2) was filtered off. An additional 1.679 g (55%) of the product (2) was collected after diluting the filtrate with 130 ml of ether and cooling to 5° C.

Example 3

This example demonstrates the synthesis of difluoroflosequinan (3-difluoromethylsulfinyl-7-fluoro-1-methyl-4-quinolone). The overall synthetic scheme is described in more detail according to the following reactions. For the purpose of this example, all bracketed numbers [e.g., "(1)"] after the chemical name of a compound refer to the corresponding chemical structure as designated by the same bracketed number in FIG. 4.

Step One: Fluorination of 7-fluoro-3-fluoromethylthio-1-methyl-4-quinolone (2) to synthesize 3-difluoromethylthio-7-fluoro-1-methyl-4-quinolone (4).

To a stirred solution-(a part remained undissolved) of crude 7-fluoro-3-fluoromethylthio-1-methyl-4-quinolone (2) (4.15 g, 17.2 mmol) in dry acetonitrile (138 ml) under a nitrogen atmosphere SELECTFLUOR [Product No. 25140; 1-chloromethyl-4-fluoro-1,4-diazoniabicyclo[2.2.2]octane bis(tetrafluoroborate)] (7.617 g, 21.5 mmol) was added in a few portions over a period of approximately 2 min. During the addition a slight cooling was applied to keep the temperature below 23° C. After 15 min of stirring at 23° C., triethylamine (3.0 ml, 2.18 g, 21.5 mmol) was added with cooling over a period of approximately 2 min. and stirring was continued at 23° C. for 10 min. The reaction mixture was poured into ice-water mixture (750 ml), and extracted with four 300 ml portions of DCM. The combined extracts were dried over a mixture of anhydrous sodium sulfate and sodium carbonate, and concentrated to give 3.43 g of a crude product, which contained less than 30% of 3-difluoromethylthio-7-fluoro-1-methyl-4-quinolone (4). The presence of the compound (4) was confirmed by a characteristic triplet observed in $^1$H NMR spectrum ($\delta$=7.10 ppm, J=58.9 Hz). The crude product was used in the second step without purification.

Step Two: Oxidation of 3-difluoromethylthio-7-fluoro-1-methyl-4-quinolone (4) to synthesize 3-difluoromethylsulfinyl-7-fluoro-1-methyl-4-quinolone (5).

To a stirred solution (a part remained undissolved) of crude 3-difluoromethylthio-7-fluoro-1-methyl-4-quinolone (4) (3.43 g, 13.23 mmol) in DCM (200 ml) at 0° C. was added ~80% MCPBA (2.50 g, 11.59 mmol) in a few portions over a period of approximately 1 min. The stirred mixture was allowed to warm to room temperature and was stirred for 30 min. An additional amount of MCPBA (640 mg) was added in 5 portions in approximately 1 h intervals, and the progress of the oxidation was monitored by $^1$H NMR 30 min after each addition. The mixture was washed with 5% aqueous $Na_2CO_3$ (70 ml), the aqueous layer was extracted with DCM (2×200 ml), the combined extracts were dried over anhydrous sodium sulfate and concentrated. The residue was chromatographed on silica gel with DCM and then with hexane-ethyl acetate (gradient 2:1,1:1,1:2).to give 980 mg (20.7%; two steps) of the product. The product was further purified by recrystallization from absolute ethanol to give 620 mg (13.1%) of 3-difluoromethylsulfinyl-7-fluoro-1-methyl-4-quinolone (5) as off-white crystals. $^1$H NMR, $CDCl_3$; $\delta$=3.94 s, 3H, N-$CH_3$; 7.050, 6.870, 6.866, 6.686 (4 lines, X part of ABX), 1H, $CHF_2$; 7.21 dd, 1H, J=10.2 & 2.4 Hz, H at C8, 7.27 ddd, 1H, J=8.9, 7.9 & 2.2 Hz, H at C6; 7.99 s, 1H, H at C2; 8.44 dd, 1H, J=9.0 & 6.3 Hz, H at C5.

Example 4

In this example racemic flosequinan is prepared according to the following protocol.

A. Preparation of Racemic Flosequinan i. Step I

In a clean and dry 12 L glass reactor equipped with a back suction trap plus a NaOH (25%) trap at the outlet and a back suction trap in the inlet, 3.840 L of toluene were charged and cooled to −45° C. using a dry ice-acetone bath. Using appropriate safety precautions, 832 g of phosgene were then passed through the cold toluene while stirring to prepare a 20% (wt/wt) solution. The addition of the phosgene took approximately 3.5 hours.

Separately, into a clean and dry 22 L glass reactor equipped with the above-described types of back suction traps, 399 g of starting material (formula I):

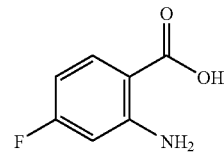

was added with stirring to 4.37 L of deionized water. A separate 6.8% solution of sodium carbonate in water was also prepared by adding 297 g of sodium carbonate to 4.37 L of deionized water. Using a clean addition funnel, the sodium carbonate solution was then slowly added with stirring to the suspension of the starting material, to create a brown-colored solution.

In preparation for the reaction step, the phosgene solution was warmed from −45° C. to −15° C. and the mixture of the starting material and the sodium carbonate was cooled to 10° C. The phosgene solution was then added over approximately 1.5 hours with stirring to the brown solution. The reaction mixture was stirred overnight allowing the desired intermediate-A (formula II):

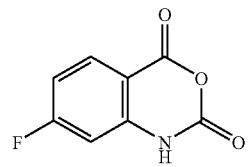

to precipitate out. A sample was removed for NMR assessment and the precipitate was filtered on a 4 L sintered glass funnel. The filtrate was washed with 2×500 ml aliquots of cold deionized water and dried under a vacuum at approximately 50° C. for 16 hours.

A 93.4% lot yield of 435 g of intermediate-A (formula II) was obtained. This procedure was repeated three more times, starting with approximately 400 g of starting material each time. Lot yields of 448 g (94.5%), 449 g (95.9%), and 459 g (96.8%) were obtained.

ii. Step II

In a 22 L oven dried glass reactor equipped with a reflex condenser, addition funnel and temperature recorder, 11.40 L of anhydrous tetrahydrofuran (THF) were added under nitrogen. To this reactor were also added 409 g of 60% sodium hydride in oil. Eight approximately equal portions of intermediate-A (formula II) were then added to the reactor, totaling 883 g altogether. As this reaction is exothermic, care was taken to avoid excessive heat and bubbling. Final temperature was 40° C., with a maximum observed temperature of 41° C. The reaction mixture was stirred until hydrogen gas evolution ceased.

To the reaction mixture was then slowly added 575 ml (766.4 g) of dimethyl sulfate, keeping the temperature below 50° C. Upon completion, the reaction mixture was stirred at 50° C. for 3 hours with the reflux condenser on. A sample was removed for NMR assessment, and the heat was turned off before stirring overnight.

In the morning, the stirring was stopped and the clear liquid on top was siphoned off. This liquid was filtered using a 2–3 inch thick Celite pad in a 2 L sintered glass funnel. The residue cake was kept covered to minimize contact with atmospheric moisture. The residue was collected and washed with 4 aliquots of anhydrous THF. The filtrate and the washings were evaporated to dryness using a rotary evaporator and the residue obtained was dried under vacuum at approximately 36–38° C. overnight. A sample was removed for NMR assessment of the amount of unreacted dimethyl sulfate present. The dried residue was then added to 1600 ml of a 1:3 toluene:hexane mixture and vigorously stirred. This mixture was then filtered and washed with 2×700 ml washings of 1:3 toluene:hexane mixture. A reference sample was removed for NMR assessment and the residue was dried at 51–50° C. under vacuum for 36 hours.

This batch yielded 871 g of intermediate-B (formula III):

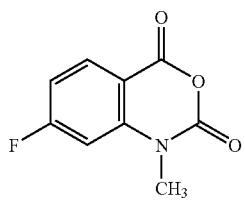

III for a lot yield of 91.6%. Another 907.1 g of intermediate-A was subjected to the procedure of step II, in which the amounts of reactants and solvents was proportionately adjusted with a yield of 850 g (87%).

iii. Step III

In an oven dried 12 L glass reactor equipped with a stirrer, temperature recorder and addition funnel, 2550 ml of anhydrous toluene was added under nitrogen. Then 236 g of 60% sodium hydride in oil was added, all at room temperature. The reaction mixture was heated with continuous stirring to 75° C. using a heating mantel. Then 1.59 L of anhydrous dimethyl sulfoxide (DMSO) were added slowly and carefully over 45 minutes taking care to avoid excessive bubbling. The reaction mixture was stirred for one hour at 70–72° C. until clear and hydrogen gas evolution ceased. The heating mantel was turned off and a water bath was used to cool the reaction mixture to 30° C.

To this mixture, 538.2 g of dry intermediate-B (formula III) was added slowly in portions, keeping the temperature no higher than 35° C. Then 1.9 L of anhydrous DMSO was added, again keeping the temperature no higher than 35° C. The reaction mixture was stirred under nitrogen for one hour, allowing the mixture to cool to 26° C. The reaction mixture was then quenched slowly and carefully with 320 ml of methanol. The resulting suspension was then added slowly and with vigorous stirring to a 22 L reaction vessel containing 12.760 L of diethyl ether.

After stirring was stopped, the upper ether layer was siphoned off and the brown oil lower layer was washed with 520 ml of fresh ether. The oily yellow residue was triturated with 2600 ml of deionized water until a yellow precipitate formed. This precipitate was filtered using a 2 L sintered glass funnel and the solid residue was washed with three aliquots of 130 ml cold deionized water. A reference sample was taken to assess the residue. The residue was dried under vacuum at 50–53° C. for 23 hours.

This procedure produced 243 g of intermediate C (formula IV):

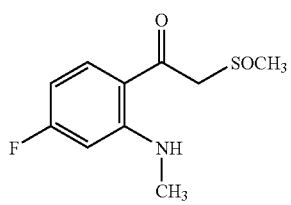

IV which represents a 38.4% yield. Two other batches of intermediate-B were treated according to this Step III procedure, with proportionate adjustments to the amounts of reactants and solvents. The first additional batch of 538.2 g intermediate-B produced a 192 g (30.4%) yield, and the second additional batch of 87.38 g of intermediate-B produced a yield of 42 g (40.9%).

iv. Step IV

In a 12 L oven dry glass reactor equipped with a stirrer, temperature recorder and addition funnel which has been dried by nitrogen flow for 30 minutes the following chemicals were charged: 7.990 L of triethyl orthoformate; 696 g of intermediate-C; 324 ml of piperdine; and 296 ml of acetic acid. The reaction mixture was heated under nitrogen to reflux at approximately 105° C. for 2 hours. A sample was removed to assess the progress of the reaction step by NMR.

Using a water bath, the reaction mixture was then cooled to room temperature and stirred for 30 minutes. The final product precipitated out and was collected by filtration on a 4 L sintered glass funnel. The residue was washed with 3×700 ml aliquots of diethyl ether, and a sample was removed for NMR assessment. The residue was dried under vacuum at 50–51° C. for 17 hours.

A sample of the dried flosequinan product (formula V):

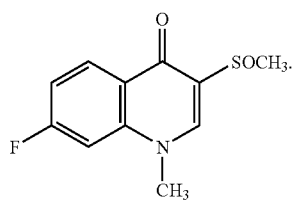

V was removed for NMR assessment. 547 g (75.3%) yield of flosequinan was obtained (an additional 47 g of product was scraped from the bottom of the sintered glass filter but was not included in this total yield calculation).

Example 5

In this example, monofluoroflosequinan was subjected to biochemical enzyme assays and radioligand binding assays to determine its percent inhibition of a variety of enzyme activities and its percent inhibition of specific binding. The methods used have been adapted from those described in the scientific literature, see Hidaka and Asano "Human blood platelet 3':5' cyclic nucleotide phosphodiesterase. Isolation of low-Km and high Km phosphodiesterase." *Biochem. Biophys. Acta* 429:485 (1976); Nicholoson et al. "Differential modulation of tissue function and therapeutic potential of selective inhibitors of cyclic nucleotide phosphodiesterase isoenzymes" *Trends Pharmacol. Sci.* 12:19 (1991); Cortijo et al. "Investigation into the role of phosphodiesterase IV in bronchorelaxation, including studies with hyman bronchus." *Br. J Pharmacol.* 108:562 (1993); Baehr et al. "Isolation and characterization of cGMP phosphodiesterase from bovine rod outer segments." *J. Biol. Chem.* 254:11669 (1979), Gillespie and Beavo "Inhibition and stimulation of photoreceptor phosphodiesterase by dipyridamole and M&B 22,948" *Molecular Pharm.* 36:773 (1989); Tamaoki and Nakano "Potent and specific inhibitors of protein kinase C of microbial origin" *Biotechnology* 8:732 (1990); Wilkinson et al. "Isoenzyme specificity of bisindolymaleimides, selective inhibitors of protein kinase C" *Biochem. J* 294:335 (1993); Tamaki et al. "Staurosporine, a potent inhibitor of phospholipid/Ca++dependent protein kinase" *Biochem. Biophys. Res. Comm,* 135:397 (1986); Schoemaker and Langer "[3H]Diltiazem binding to calcium channel antagonist recognition sites in rate cerebral cortex" *Eur. J Pharmacol.* 111:273 (1985); Ehlert et al. "The binding of [3H]nitrendipine to receptors for calcium channel antagonists in the heart, cerebral cortex and ileum of rats." *Life Sci.* 30:2191 (1982); Gould et al. "[3H]nitrendipine-labeled calcium channels discriminate inorganic calcium agonists and antagonists" *Proc. Natl. Acad. Sci. USA* 79:3656 (1982); Reynolds et al. "(−)-[3H]Desmethoxyverapamil labels multiple calcium channel modulator receptors in brain and skeletal muscle membranes: Differentiation by temperature and dihydropyridines" *J Pharmacol. Exp. Ther.* 237:731 (1986) and Worley et al. "Characterization of inositol triphosphate receptor binding in brain. Regulation by pH and calcium" *J Biol. Chem.* 262:12132 (1987). A brief summary of the conditions for each assay is provided below:

PDE1: PDE1 partially purified from bovine heart was used. The compound was incubated with 13 µg PDE1 enzyme, 1.01 µM [3H]cAMP+cAMP and $CaCl_2$/calmodulin in Tris buffer pH 7.5 for 20 minutes at 25° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [3H]adenosine in the aqueous phase was quantitated by scintillation counting.

PDE2: PDE2 partially purified from human platelets was used. The compound was incubated with 23 µg PDE2 enzyme, 25.1 µM [3H]cAMP+cAMP in Tris buffer pH 7.5 for 20 minutes at 25° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [3H]adenosine in the aqueous phase was quantitated by scintillation counting.

PDE3: PDE3 partially purified from human platelets was used. The compound was incubated with 13 µg PDE3 enzyme and 1.01 µM [3H]cAMP+cAMP in Tris buffer pH 7.5 for 20 minutes at 25° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [3H]adenosine in the aqueous phase was quantitated by scintillation counting.

PDE4: PDE4 partially purified from human U-937 pronocytic cells was used. The compound was incubated with 20 µg PDE4 enzyme and 1.01 µM [3H]cAMP+cAMP in Tris buffer pH 7.5 for 20 minutes at 25° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [3H]adenosine in the aqueous phase was quantitated by scintillation counting.

PDE5: PDE5 partially purified from human platelets was used. The compound was incubated with 120 µg PDE5 enzyme and 1.01 µM [3H]cGMP+cGMP in Tris buffer pH 7.5 for 20 minutes at 25° C. The reaction was terminated by boiling for 2 minutes, and the resulting GMP was converted to guanosine by addition of 10 mg/ml snake venom nucleotidase and further incubation at 30° C. for 10 minutes. Unhydrolyzed cGMP was bound to AGI-X2 resin, and the remaining [3H]guanosine in the aqueous phase was quantitated by scintillation counting.

PDE6: PDE6 partially purified from bovine retinal rod outer segments and activated by trypsin was used. The compound was incubated with 0.2 µg/ml active PDE6 and 100 µM [3H]cGMP+cGMP in Tris buffer pH 7.5 for 20 minutes at 25° C. Each reaction was terminated by boiling for 2 minutes. The resulting GMP was converted to guanosine by addition of 10 mg/ml snake venom nucleotidase, and further incubated at 30° C. for 10 minutes. Unhydrolyzed cGMP was bound to AGI-X2 resin, and [3H]guanosine remaining in the aqueous phase was quantitated by scintillation counting.

Protein Serine/Threonine Kinase PKCα: Human recombinant enzyme from Sf9 insect cells was used in the assay. The substrate was 200 µg/ml histone. The reaction was incubated 10 mins at 25° C. in 20 mM Hepes, 10 mM $MgCl_2$, 0.1 mM $CaCl_2$. [32P]histone was quantitated.

Protein Serine/Threonine Kinase PKC, Non-Selective: The enzyme was obtained from rat brain and the substrate was 370 µg/ml histone. The reaction was pre-incubated 5 min at 25° C., followed by a 15 min incubation at 25° C. in a buffer of 20 mM Tris-HCl, 10 mM $MgCl_2.H_o$ and 0.1 mM $CaCl_2.2H_O$, pH 7.4. [32P]histone was quantitated.

The radioligand binding assays are briefly summarized below: Calcium Channel Type L, Benzothiazepine:

The source was Wistar rat brain and the ligand was 2 nM 3H Diltiazem. The incubation was for 3 hr at 4° C. in 50 mM Tris-HCl, 0.1% BSA, pH 7.4 (buffer at 25° C.). The nonspecific ligand was 10 µM Diltiazem. The following are historical values: $K_d$: 0.016 µM, $B_{max}$: 0.21 pmol/mg protein, specific binding: 73%. Radioligand binding was quantitated.

Calcium Channel Type L, Dihydropyridine: The source was Wistar rat cerebral cortex and the ligand was 0.1 nM 3H Nitrendipine. The incubation was for 90 min at 25° C. in 50 mM Tris-HCl, pH 7.7. The nonspecific ligand was 1 µM Nifedipine. The following are historical values: $K_d$: 0.18 nM, $B_{max}$: 0.23 pmol/mg protein, specific binding: 91%. Radioligand binding was quantitated.

Calcium Channel Type L, Phenylalkylamine: The source was Wistar rat brain and the ligand was 0.4 nM 3H (−)-D-888. The incubation was 60 min at 25° C. in 50 mM Hepes, pH 7.4. The nonspecific ligand was 10 µM (−)-D-600. The following are historical values: $K_d$: 0.014 µM, Bmax: 1.6 pmol/mg protein, specific binding: 80%. Radioligand binding was quantitated.

Inositol Triphosphate, $IP_3$: The source was Wistar rat cerebellum and the ligand was 2.5 nM 3H 1,4,5-$IP_3$. The incubation was 10 min at 25° C. in 50 mM Tris-HCl, 1 mM EDTA, 0.1% BSA, pH 8.3. The nonspecific ligand was 1 µM 1,4,5-$IP_3$. The following are historical values: $K_d$: 0.066 µM, $B_{max}$: 3.5 pmol/mg protein, specific binding 85%. Radioligand binding was quantitated.

FIG. 5 depicts the results for the assays described above. For the PDE inhibition assays, monofluoroflosequinan was used at a concentration of 100 μM (in 1% DMSO as the vehicle). For the protein kinase assays, monofluoroflosequinan was used at a concentration of 1000 μM (in 1% DMSO as the vehicle). For the protein serine/threonine kinase (PKC, non-selective), monofluoroflosequinan was also tested at 300 μM and 100 μM. For the radioligand binding assays, monofluoroflosequinan was used at a concentration of 1000 μM (in 0.4% DMSO as the vehicle). Significant inhibition of protein serine/threonine kinase, PKC, non-selective was observed at 1000 μM, 300 μM and 100 μM monofluoroflosequinan (See FIG. 5).

Figure 7:
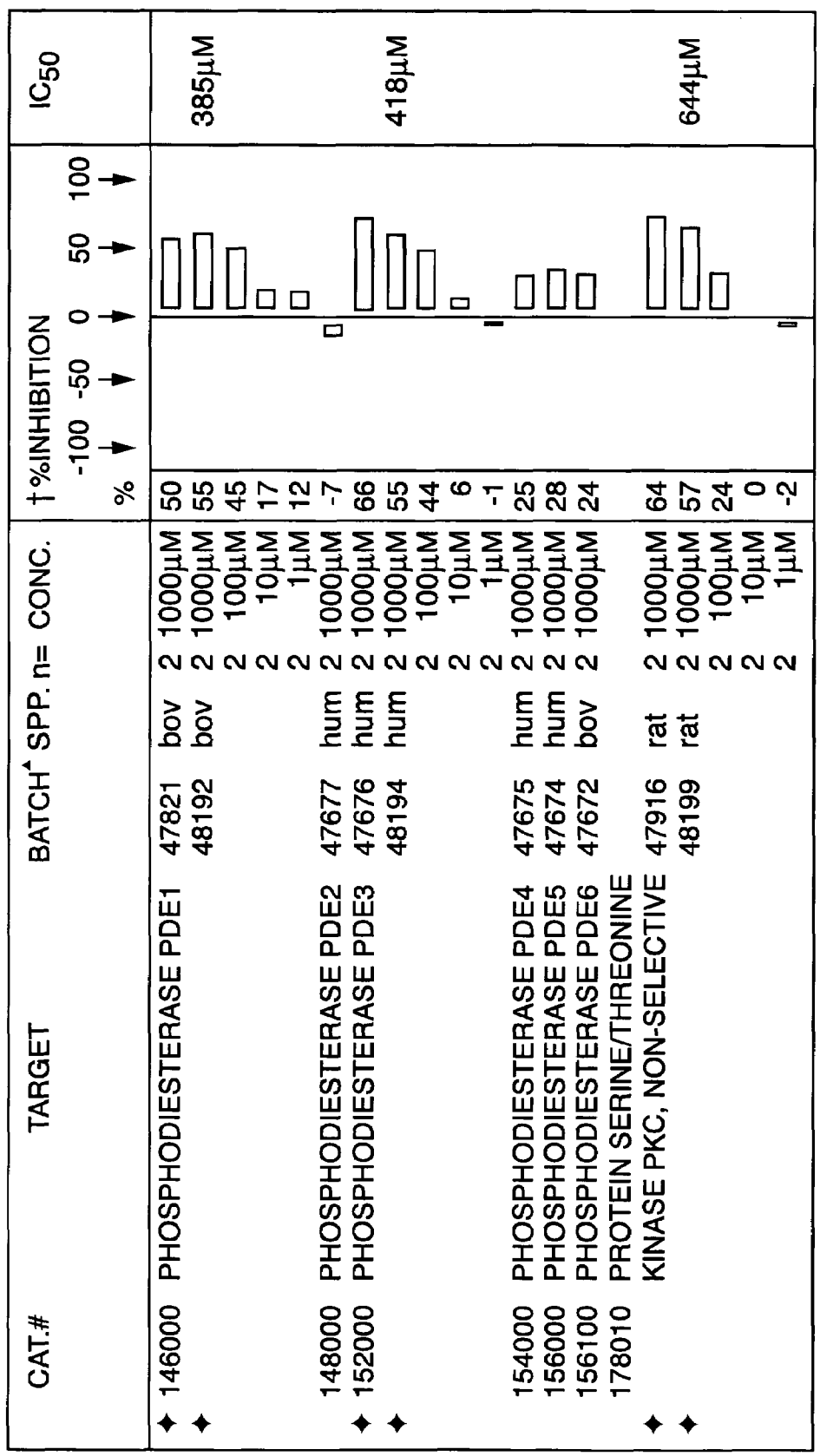
FIG. 7 depicts the results of enzyme inhibition and radioligand binding assays with the sulfone derivative of difluoroflosequinan (e.g., 3-difluoromethylsulfonyl-7-fluoro-1-methyl-4-quinolone).

FIG. 7 projects data for the sulfone derivative of difluoroflosequinan (e.g., 3-difluoromethylsulfonyl-7-fluoro-1-methyl-4-quinolone) in the assays described above. For the PDE inhibition assays, 3-difluoromethylsulfonyl-7-fluoro-1-methyl-4-quinolone was used in varying concentrations (in 1% DMSO as the vehicle). For the protein kinase assays, monofluoroflosequinan was used at a concentration of 1000 μM (in 1% DMSO as the vehicle). For the protein serine/threonine kinase (PKC, non-selective), 3-difluoromethylsulfonyl-7-fluoro-1-methyl-4-quinolone was tested at a concentration of 1000 μM. Significant (e.g., greater than 50%) inhibition of PDE1, PDE3, and PDE4 was observed at a 3-difluoromethylsulfonyl-7-fluoro-1-methyl-4-quinolone of 1000 μM. (See FIG. 7).

Figure 8:
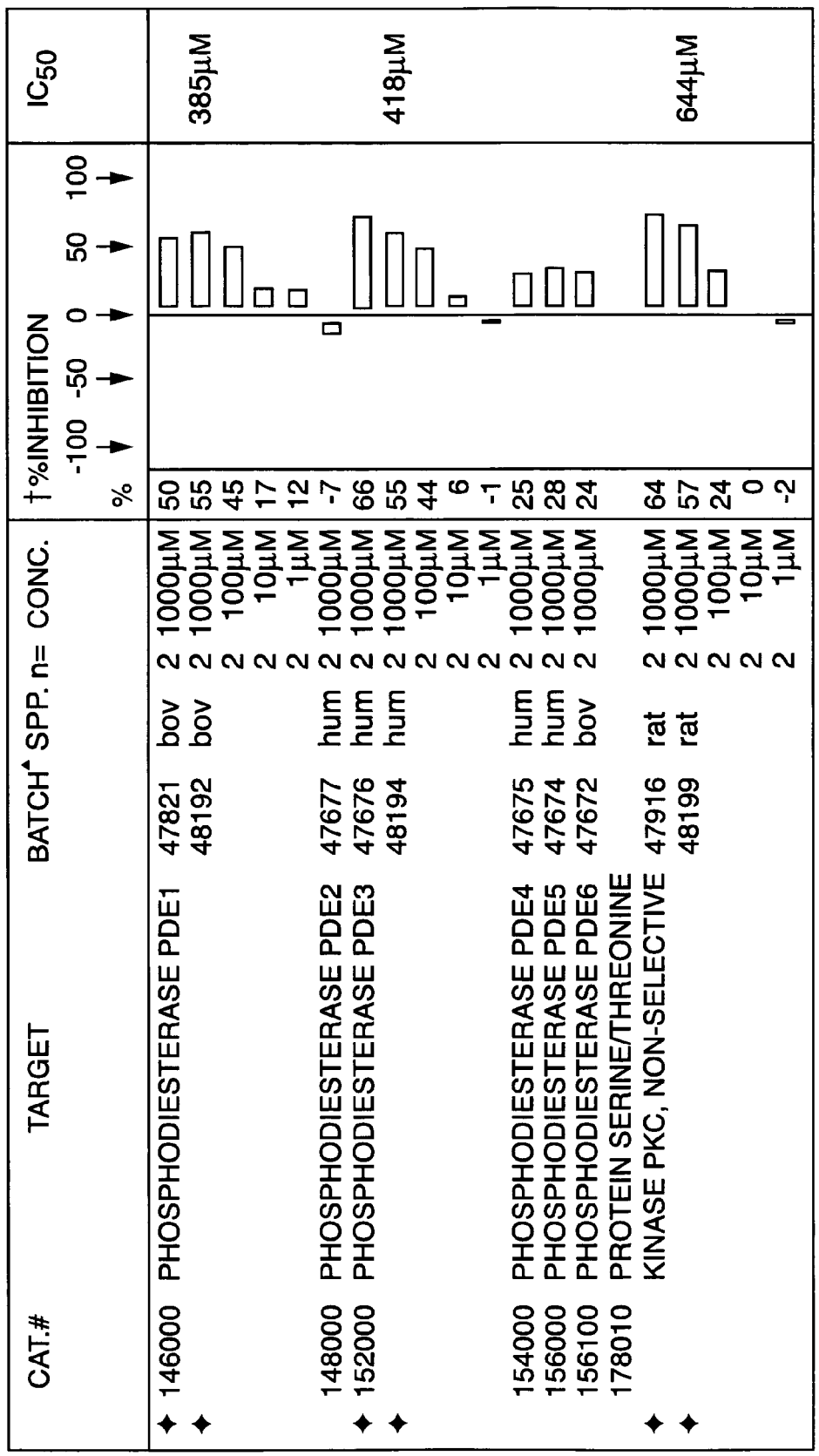
FIG. 8 depicts the results of enzyme inhibition and radioligand binding assays with difluoroflosequinan (e.g., 3-difluoromethylsulfinyl-7-fluoro-1-methyl-4-quinolone).

FIG. 8 projects data for difluoroflosequinan (e.g., 3-difluoromethylsulfinyl-7-fluoro-1-methyl-4-quinolone) in the assays described above. For the PDE inhibition assays, 3-difluoromethylsulfinyl-7-fluoro-1-methyl-4-quinolone was used in varying concentrations (in 1% DMSO as the vehicle). For the protein kinase assays, monofluoroflosequinan was used at a concentration of 1000 μM (in 1% DMSO as the vehicle). For the protein serine/threonine kinase (PKC, non-selective), 3-difluoromethylsulfinyl-7-fluoro-1-methyl-4-quinolone was tested at a concentration of 1000 μM. Significant (e.g., greater than 50%) inhibition of PDE1, PDE3, and protein serine/threonine kinase (PKC, non-selective) was observed at a 3-difluoromethylsulfinyl-7-fluoro-1-methyl-4-quinolone concentration of 1000 μM. (See FIG. 8).

Example 6

Synthesis of the sulfone derivative of difluoroflosequinan.

This overall synthetic scheme is described in more detail according to the following reactions. For the purpose of this example, all bracketed numbers [e.g., "($_1$)"], after the chemical name of a compound, refer to the corresponding chemical structure as designated by the same bracketed number in FIG. 6.

To a solution of 3-difluoromethylsulfinyl-7-fluoro-1-methyl-4-quinolone (5) (79 mg, 0.287 mmol) in DCM (8 mL) was added 80% MCPBA (55.7 mg, 0.258 mmol). The mixture was stirred at a room temperature overnight. An additional amount of MCPBA (15 mg) was added and stirring was continued for 3 days. The mixture was diluted with DCM (10 mL), washed with 5% aqueous $Na_2CO_3$ (3×5 mL), the aqueous layers were extracted with DCM (2×10 mL), the combined organic extracts were dried over anhydrous sodium sulfate and concentrated. The residue, e.g., the crude product, was recrystallized from ethyl acetate to give 27 mg (32%) of white crystals [3-difluoromethyl sulfonyl-7-fluoro-1-methyl-4-quinolone (6)]. The filtrate was chromatographed on silica gel with ethyl acetate-hexane (gradient 1:2, 1:1) to give second crop of the product [3-difluoromethylsulfonyl-7-fluoro-1-methyl-4-quinolone (6)] (32 mg, 38%) for a total yield 70%. This 3-difluoromethylsulfonyl-7-fluoro-1-methyl-4-quinolone gave the following NMR profile:

$^1$H NMR, $CDCl_3$; δ=3.94 s, 3H, N-$CH_3$; 6.85 t,1H, J=54.3 Hz, $CHF_2$; 7.21 dd, 1H, J=9.7 & 2.2 Hz, H at C8, 7.35-7.26 m, 1H, H at C6; 8.41 s, 1H, H at C2; 8.49 dd, 1H, J=8.8 & 6.1 Hz, H at C5.

All publications and patents mentioned in the above specification are herein incorporated by reference. Various modifications and variations of the described invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A composition comprising the sulfone derivative of difluoroflosequinan, said sulfone derivative of difluoroflosequinan having the structure:

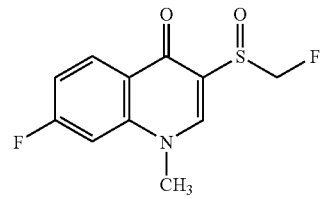

2. A method for the synthesis of 3-difluoromethylsulfonyl-7-fluoro-1-methyl-4-quinolone, comprising:
  a) providing:
    i) 3-difluoromethylsulfinyl-7-fluoro-1-methyl-4-quinolone, and
    ii) m-chloroperbenzoic acid (MCPBA); and
  b) reacting said 3-difluoromethylsulfinyl-7-fluoro-1-methyl-4-quinolone and m-chloroperbenzoic acid (MCPBA) under conditions such that 3-difluoromethylsulfonyl-7-fluoro-1-methyl-4-quinolone is produced.

* * * * *